United States Patent [19]

Yamaguchi

[11] Patent Number: 4,566,437
[45] Date of Patent: Jan. 28, 1986

[54] ENDOSCOPE

[75] Inventor: Tatuya Yamaguchi, Tokyo, Japan

[73] Assignee: Olympus Optical Co., Ltd., Tokyo, Japan

[21] Appl. No.: 605,991

[22] Filed: May 2, 1984

Related U.S. Application Data

[63] Continuation of Ser. No. 371,271, Apr. 23, 1982, abandoned.

[30] Foreign Application Priority Data

May 1, 1981 [JP] Japan ................................. 56-66541

[51] Int. Cl.⁴ ............................................. A61B 1/00
[52] U.S. Cl. ........................................................ 128/4
[58] Field of Search ........................................ 128/4-8

[56] References Cited

U.S. PATENT DOCUMENTS

| | | | |
|---|---|---|---|
| 1,551,770 | 9/1925 | Palmeter | 128/6 |
| 3,897,775 | 8/1975 | Furihata | 128/4 |
| 4,146,019 | 3/1979 | Bass et al. | 128/6 |
| 4,224,929 | 9/1980 | Furihata | 128/6 |
| 4,261,343 | 4/1981 | Ouchi et al. | 128/4 |
| 4,270,525 | 6/1981 | Furihata | 128/4 |

Primary Examiner—Edward M. Coven
Assistant Examiner—Max F. Hindenburg

[57] ABSTRACT

The main body of the operation section comprises a holding portion which can be gripped by a single hand, and a mounting surface to which are mounted operating buttons depressed in the direction of the axes thereof. The operating buttons are aligned in the direction of the axis of the holding portion. The axis of each of the operating buttons makes an angle of more than 90° to 150° with the axis of the holding portion as viewed from the holding portion. Also, the axes of the operating buttons get nearer toward the axis of the holding portion and make an acute angle.

4 Claims, 7 Drawing Figures

ENDOSCOPE

This application is a continuation of application Ser. No. 371,271, filed Apr. 23, 1982, abandoned 5/2/84.

BACKGROUND OF THE INVENTION

This invention relates to an endoscope provided with an operating section for controlling the flowing and sucking of air, water, or the like.

The operating section of the conventional endoscope is provided with a holding portion which can be gripped by a single hand of the operator and an eyepiece section mounted to the upper edge of the operating section. Also, a plurality of operating buttons for controlling the flowing and sucking of air, water, etc. are mounted to the side wall of the operating section between the eyepiece section and the holding portion of the operating section. Each of the operating buttons is depressed in a direction perpendicular to the axis of the holding portion.

When the endoscope of the above-noted construction is operated, the holding portion is gripped by three fingers, i.e., second finger, third finger and little finger, of the left hand of the operator, with the knob mounted to the operating section for the bending operation of the insert section operated by the thumb and the operating buttons handled by the first finger. What should be noted is that the plurality of operating buttons are handled by the first finger alone of the operator. Specifically, the opening degree of the first finger from the second finger is properly adjusted for the first finger to depress selectively the operating buttons. Naturally, the first finger is bent at the first joint, i.e., joint nearest to the finger tip, and at the second joint for depressing the operating button. It should be noted in this connection that the bending direction of the finger tip depends on the opening degree of the first finger from the second finger. Naturally, the bending direction of the finger tip does not conform with the depressing direction of the button depending on the opening degree of the first finger. It follows that the first finger must be moved unnaturally, leading to accumulation of fatigue.

SUMMARY OF THE INVENTION

An object of the present invention is to provide an endoscope which permits the operating buttons to be depressed easily without requiring an unnatural movement of the finger serving to depress the buttons.

According to the present invention, there is provided an endoscope, in which an operating button mounted to the mounting surface of the operating section extends toward the central axis of the holding portion of the operating section, and the central axis along which the operating button is depressed makes an angle of more than 90° to 150° with the axis of the holding portion as viewed from the holding portion.

DETAILED DESCRIPTION OF THE PREFERRED EMBODIMENTS

Figure 1:
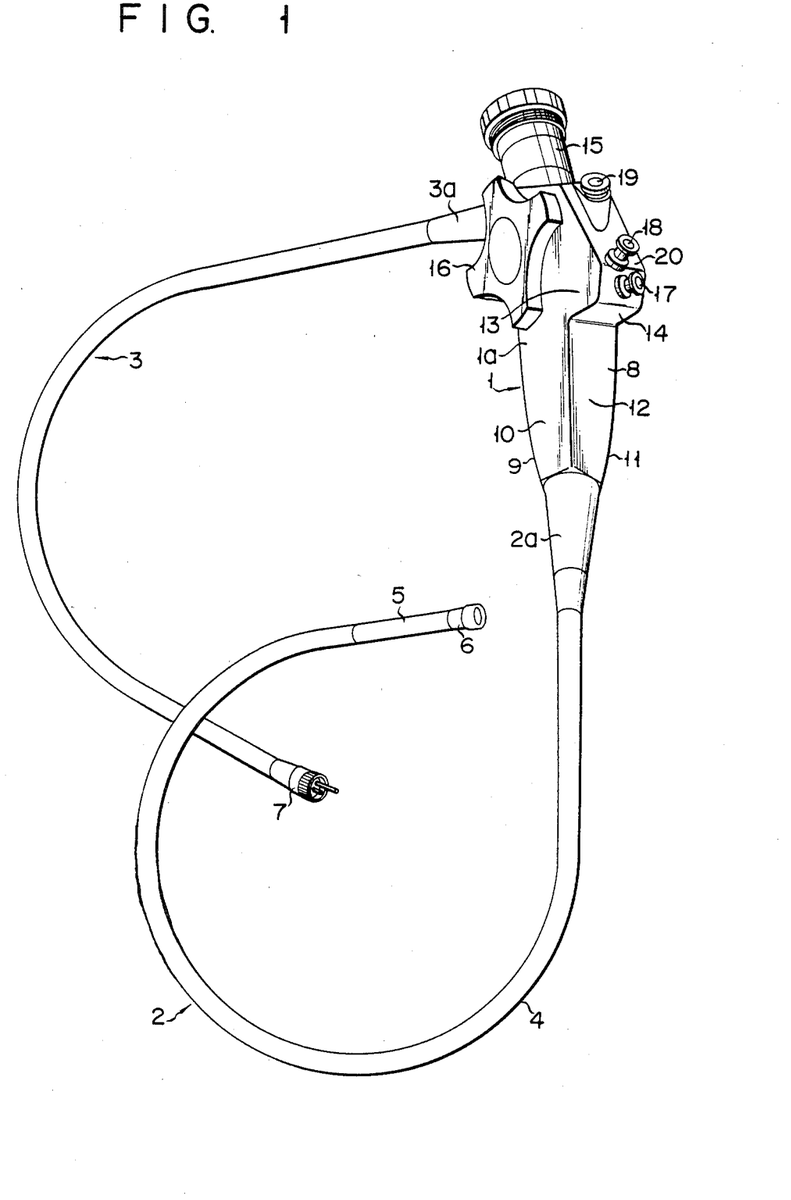
FIG. 1 is an oblique view showing an endoscope according to one embodiment of the present invention.

FIG. 1 shows an endoscope according to one embodiment of the present invention. It is seen that the endoscope comprises an operating section 1, an insert section 2 which is to be inserted into the body cavity of a patient, and a universal cord 3 for guiding a light guide fiber (not shown). The insert section 2 consists of a flexible tube 4, a rigid tip portion 6, and a bending tube 5 disposed between the flexible tube 4 and the rigid tip portion 6. Connected to the free end of the universal cord 3 is a socket 7 for connecting the universal cord 3 to an illumination light source device (not shown).

The operating section 1 comprises a main body 1a which is substantially of parallel piped shape. Specifically, the main body 1a comprises a front surface 8, a rear surface 9, a right side surface 10, and a left side surface 11. The lower half of the main body 1a constitutes a holding portion 12 which can be gripped by a single hand of the operator. It is seen that the upper half of the front surface 8 is projected forward so as to form a projecting portion 13. Naturally, a rising wall 14 is formed at the boundary between the holding portion 12 and the projecting portion 13. As described later, the side region of the second finger is allowed to abut against the rising wall 14 so as to determine the proper position of the left hand 21 of the operator gripping the holding portion 12.

Figure 2:
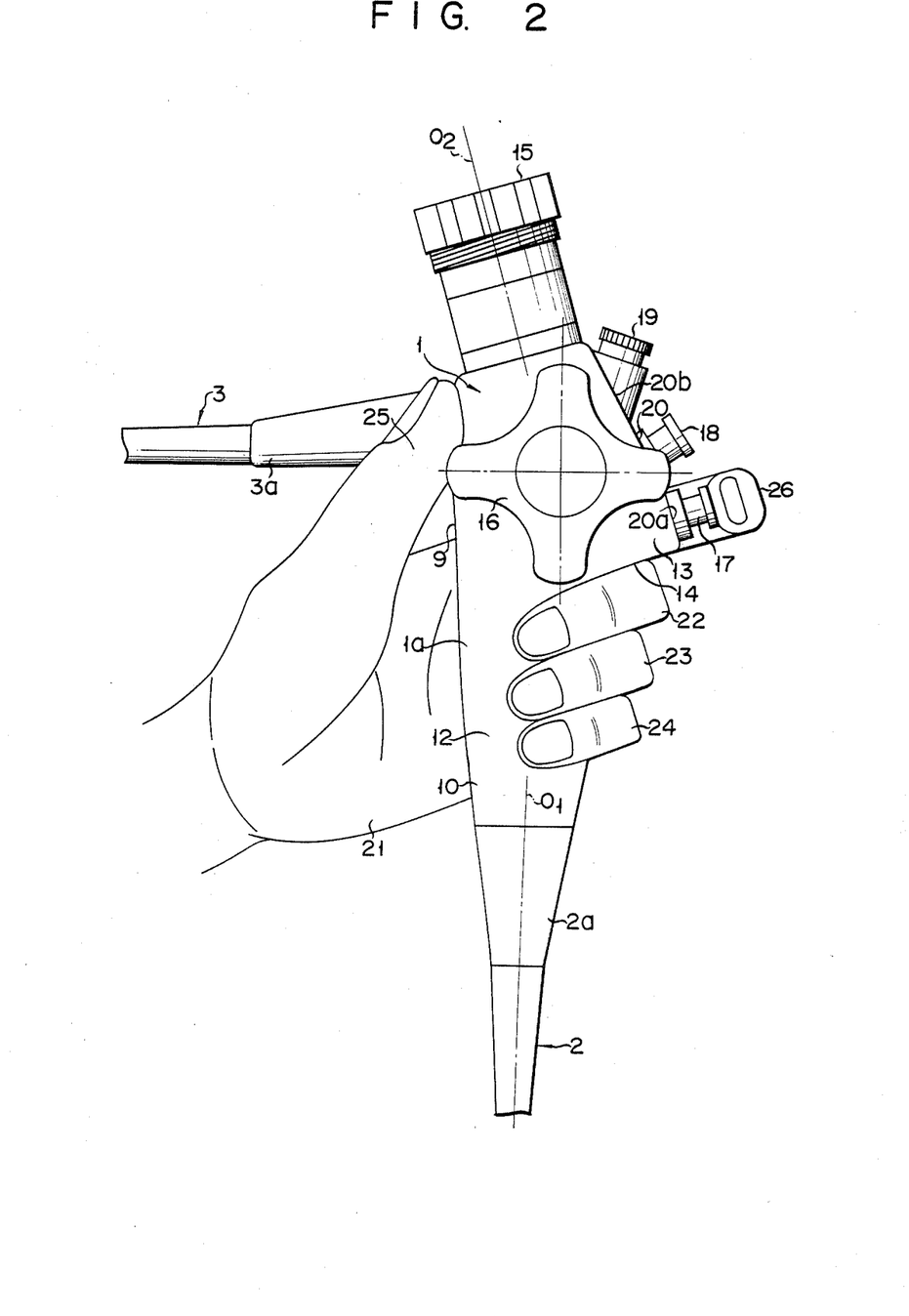
FIG. 2 is a side view showing how the operating section of the endoscope shown in FIG. 1 is gripped by the operator.

As shown in FIG. 2, the proximal end of the insert section 2 is connected via a connecting cylinder 2a to the lower end of the holding section 12 such that the axis of the connecting cylinder 2a is aligned with the central axis $O_1$ of the holding portion 12. Also, an eyepiece section 15 is mounted to the upper end of the main body 1a of the operating section 1. It should be noted that the eyepiece section 15 is inclined toward the rear surface 9 of the main body 1a such that the optical axis $O_2$ of the eyepiece section 15 makes a prescribed angle $\theta_0$, e.g., 5° to 30°, with the axis $O_1$ of the holding portion 12. An operating knob 16 for controlling the bending tube 5 of the insert section 2 is mounted to the upper portion of the right side surface 10 of the main body 1a. The operating knob 16 is mounted to a shaft 16a (see FIG. 3). The universal cord 3 is connected via a connecting tube 3a to the upper portion of the rear surface 9 of the main body 1a. It should be noted that the front surface of the projecting portion 13 constitutes a mounting surface 20. Mounted on the mounting surface 20 are a first operating button 17 for controlling the flowing of air and water into the insert section 2, a second operating button 18 for the section control, and a mouthpiece 19 for inserting a treating tool such as forceps into the insert section 2. These operating buttons 17, 18 and the mouthpiece 19 are "substantially" aligned along the axis $O_1$ of the holding portion 12 so as to enable the buttons 17, 18 to be independently depressed easily by the tip of the first finger of the operator's hand gripping the holding portion 12. The term "substantially" implies that a perfect alignment is not absolutely required as far as the buttons 17, 18 are positioned to be independently depressed easily by the finger tip mentioned above.

Figure 3:
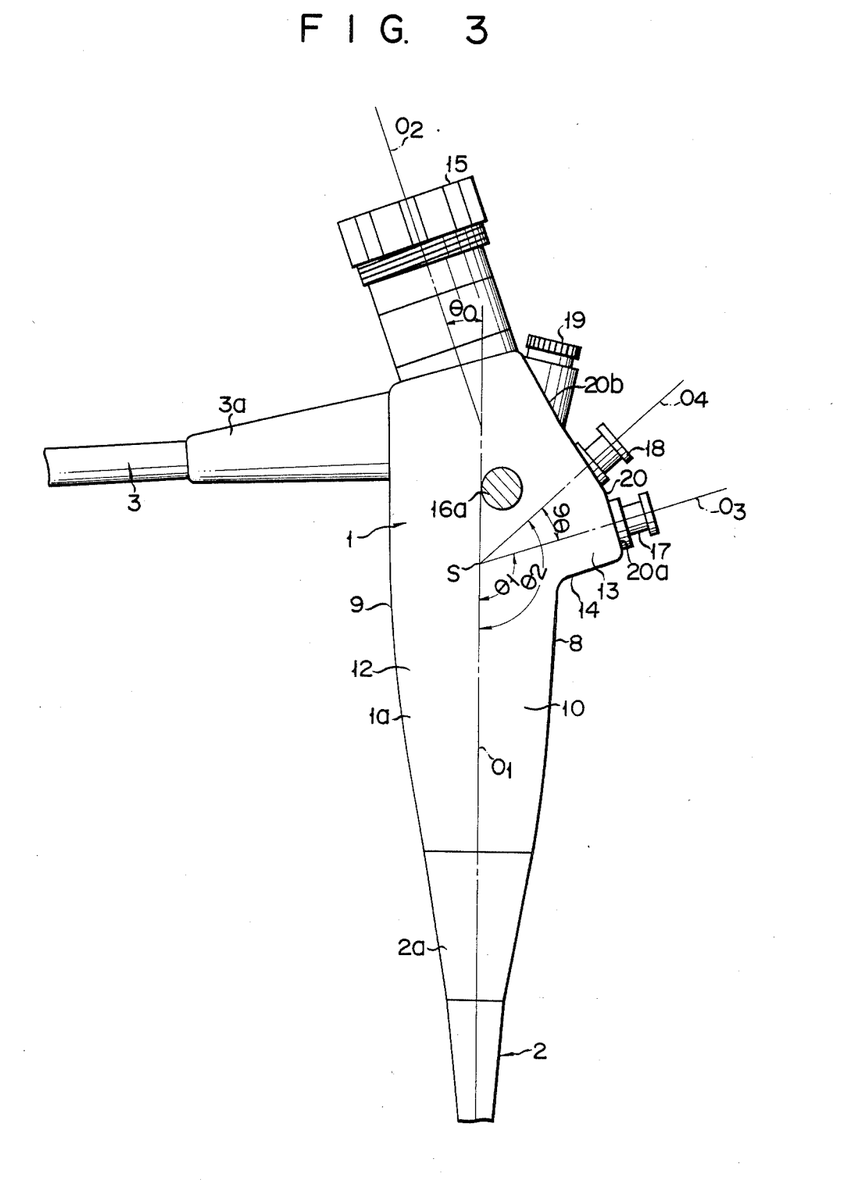
FIG. 3 is a side view equal to that of FIG. 2 except that an angle controlling knob has been removed from the operating section.

As seen from FIG. 3, the mounting surface 20 consists of a top portion 20a adjacent to the rising wall 14 and an inclined portion 20b inclined toward the eyepiece section 15. The top portion 20a is perpendicular to the depressing direction of the first operating button 17. On the other hand, the inclined portion 20b is substantially perpendicular to the depressing direction of the second operating button 18. It is important to note that the central axis $O_3$ of the button 17 along which the button 17 is depressed makes an angle $\theta_1$ of 105° with the axis $O_1$ of the holding portion 12. Also, the central axis $O_4$ of the button 18 along which the button 18 is depressed makes an angle $\theta_2$ of 125° with the axis $O_1$ of the holding portion 12. Further, the axes $O_3$ and $O_4$ cross each other at a point S on the axis $O_1$ of the holding portion 12. In other words, the axes $O_3$ and $O_4$ get nearer to each other toward the axis $O_1$ of the holding portion 12 and make an acute angle $\theta_6$. Incidentally, the axes $O_1$, $O_3$ and $O_4$ do not necessarily lie on a single plane, namely, these axes do not necessarily cross each other. The angle $\theta_6$ is chosen to fall within the range of, for example, between 5° and 20° in view of the distances of the buttons 17, 18 from the cross point S, the sizes of the buttons 17, 18, etc. such that the buttons 17, 18 can be depressed independently.

The first operating button 17 serves to operate a valve (not shown) mounted within the main body 1a for switching the air and water flowing operations. The switching valve mentioned above serves to open and close selectively an air passage and a water passage provided within the endoscope so as to introduce air and water selectively into the body cavity. Incidentally, the construction of the switching valve is described in detail in U.S. Pat. No. 3,903,877 and U.S. Pat. No. 4,261,343.

The second operating valve 18 serves to operate a suction switching valve (not shown) mounted within the main body 1a. The suction switching valve is provided midway of a suction tube (not shown) communicating with a channel provided within the endoscope for the insertion of the treating tool. Incidentally, the channel mentioned above communicates with the mouthpiece 19. The suction switching valve is opened, when necessary, so as to suck the liquid or gas within the body cavity through the suction tube and the channel. Incidentally, the construction of the suction switching valve is described in detail in U.S. Pat. No. 3,903,877 and U.S. Pat. No. 4,261,343.

Figure 4:
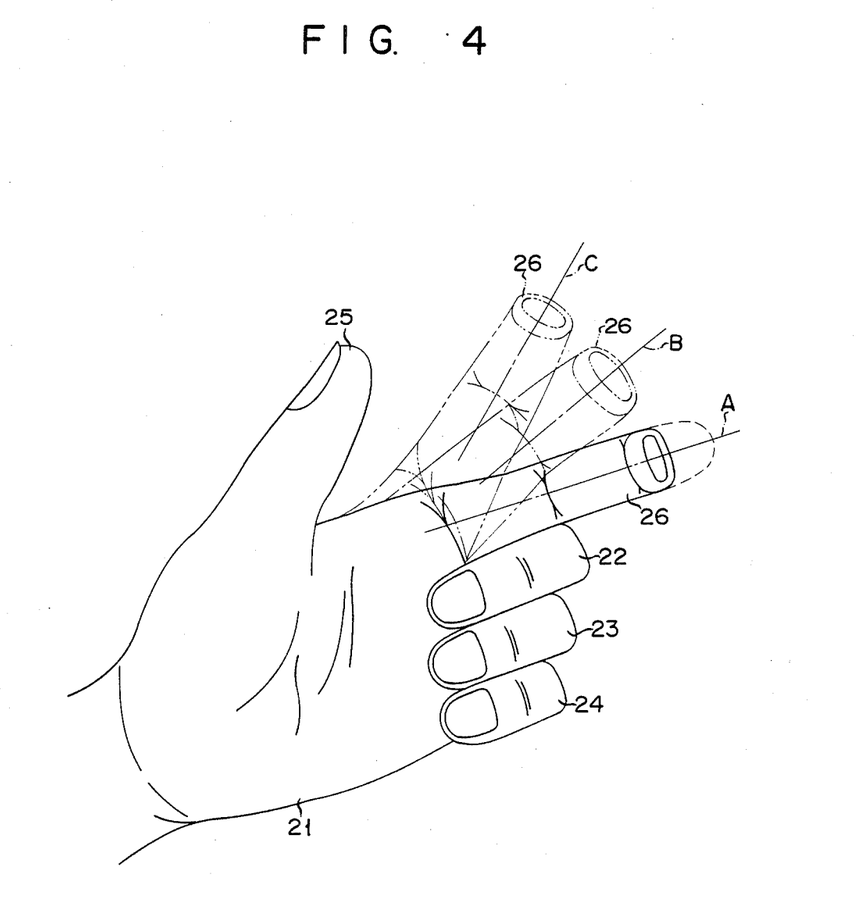
FIG. 4 is an oblique view showing the left hand of an operator.

In operating the endoscope of the construction described above, the holding portion 12 of the operating section 1 is gripped by the second finger 22, third finger 23 and little finger 24 of the operator's left hand 21 as shown in FIG. 2. Under the gripped condition, the front surface 8 is located most away from the operator's chest. As seen from the drawing, the operating knob 16 is handled by the thumb 25, and the first finger 26 is bent at the first and second joints so as to allow the finger tip to depress the operating buttons 17, 18 selectively. For depressing the first operating button 17, the first finger 26 is scarcely opened sideward from the second finger 22 as apparent from FIG. 2. In this case, the depressing direction A of the first finger 26 substantially corresponds to the axis $O_3$ of the button 17 as seen from FIG. 4, with the result that the button 17 can be depressed easily. For depressing the second operating button 18, the first finger 26 is opened sideward from the second finger 22. In this case, the depressing direction B of the first finger 26 also corresponds substantially to the axis $O_4$ of the button 18 because the axis $O_4$ makes an angle of 125° with the axis $O_1$ of the holding portion 12 as mentioned previously. It follows that the second operating button 18 can also be depressed smoothly without requiring an unnatural movement of the first finger 26.

It should also be noted that the third joint, i.e., joint at the root, of the first finger 26 substantially corresponds to the cross point S of the axes $O_3$ and $O_4$ of the buttons 17, 18. Since the finger is moved sideward about the third joint, the depressing directions A and B of the first finger 26 substantially correspond to the axes $O_3$ and $O_4$ of the buttons 17, 18, respectively, leading to a good operability of the buttons. Further, the eyepiece section 15 is inclined toward the operator from the holding portion 12, with the result that the operator is enabled to look into the eyepiece section 15 easily.

Figure 5:
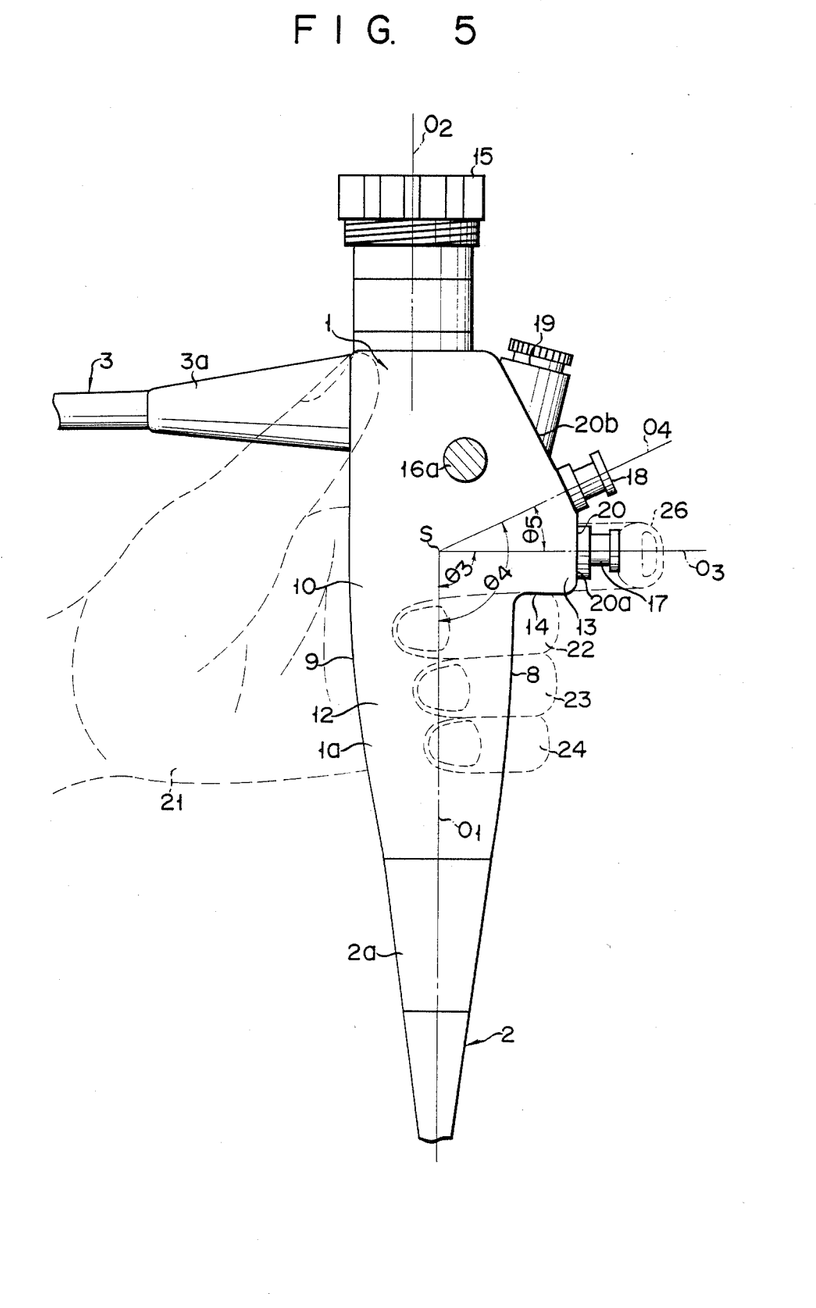
FIGS. 5 to 7 are side views each showing the operating section, from which an angle controlling knob has been removed, of an endoscope according to another embodiment of the present invention.

FIG. 5 shows another embodiment of the present invention. In this embodiment, the axes $O_3$ and $O_4$ of the buttons 17, 18 cross with the axis $O_1$ of the holding portion 12 at 90° and 110°, respectively. Also, the axis $O_2$ of the eyepiece section 15 is substantially parallel with the axis $O_1$ of the holding portion 12. As apparent from the drawing, the first finger 26 is kept in contact with the second finger 22 when the first operating button 17 is depressed by the tip of the first finger 26, resulting in an easy depression of the button 17. When the second operating button 18 is depressed, the first finger 26 is moved sideward. Since the third joint of the first finger 26 substantially corresponds to the cross point S of the axes $O_3$ and $O_4$ as apparent from FIG. 5, the depressing direction of the tip of the first finger 26 substantially corresponds to the axis $O_4$ of the second operating button 18. It follows that the button 18 can be depressed easily without requiring an unnatural movement of the first finger 26.

Figure 6:
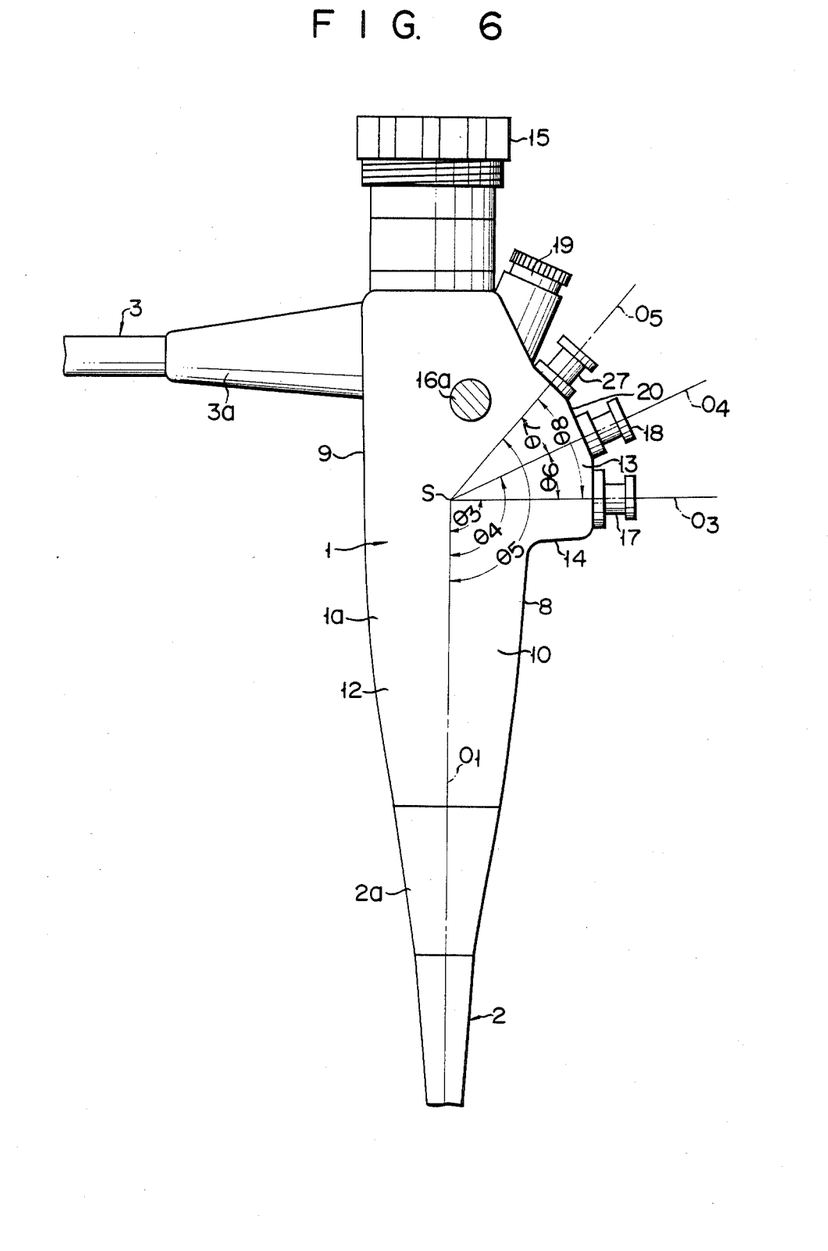

FIG. 6 shows another embodiment of the present invention. This embodiment is substantially equal in construction to the embodiment of FIG. 5, except that a third operating button 27 is mounted above the second operating button 18. The central axis $O_5$ of the third operating button 27, which serves to control, for example, the flowing of $CO_2$ gas, makes an angle $\theta_5$ of about 130° with the axis $O_1$ of the holding portion 12. It should be noted that the axes $O_4$ and $O_5$ of the buttons 18 and 27 cross each other at the point S at an acute angle $\theta_7$. Likewise, the axes $O_3$ and $O_5$ of the buttons 17 and 27 cross each other at the point S at an acute angle $\theta_8$. Incidentally, the angle $\theta_6$ made between the axes $O_3$ and $O_4$ of the buttons 17 and 18 is equal to the angle $\theta_7$ mentioned above. Of course, the third joint of the first finger substantially corresponds to the cross point S of the axes $O_3$ to $O_5$ as in the previous embodiments. It follows that the depressing direction C of the tip of the first finger 26 substantially corresponds to the axis $O_5$ of the third operating button 27, with the result that the button 27 can also be depressed easily. Of course, the buttons 17 and 18 can be depressed easily as in the embodiment of FIG. 5.

The third operating button 27 serves to operate a valve (not shown) mounted within the main body 1a for flowing a gas. The valve mentioned above, which is provided midway of a gas passage formed within the endoscope, is opened when necessary so as to flow a gas into the body cavity. The construction of the valve in question is described in detail in Japanese Utility Model Disclosure (Kokai) No. 55-143809.

Figure 7:
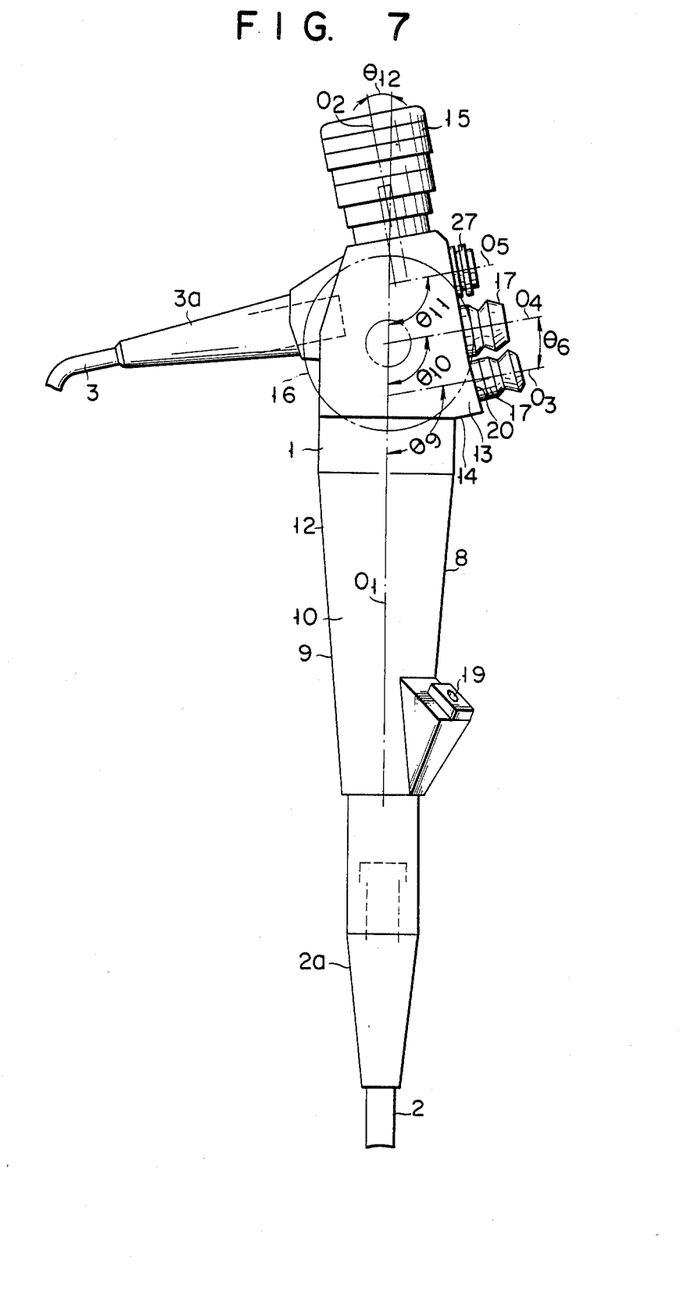

FIG. 7 shows still another embodiment of the present invention. In this embodiment, the axes $O_3$, $O_4$ and $O_5$ of the operating buttons 17, 18 and 27 are parallel with each other and each of these axes make an angle of 102° with the axis $O_1$ of the holding portion 12. Naturally, the angle of 102° mentioned above falls within the range of between more than 90° and 150° defined in the present invention. Also, the axis $O_2$ of the eyepiece section 15 makes an angle $\theta_{12}$ of 12° with the axis $O_1$ of the holding portion 12. Further, the mouthpiece 19 is mounted to the lower portion of the holding portion 12 in the embodiment of FIG. 7. The mounting surface 20 has a first end adjacent to rising wall 14 and a second end adjacent to the eyepiece section 15 and is inclined toward the central axis $O_1$ so that the second end is located closer to the central axis $O_1$ than the first end. The operating buttons are mounted on the mounting surface to extend outwardly from that mounting surface so that the operating button farther from the rising wall has a height with respect to central axis $O_1$ as measured along the axis $O_4$ which is lower than the height of the button which is closer to the rising wall as measured from central axis $O_1$ and which is measured along the axis $O_3$.

In order to make the operating section 1 small and light in the embodiment of FIG. 7, the operating buttons 17, 18, 27 and the internal mechanism operated by the operating knob 16 should be disposed close to each other. Also, the operating knob 16 is handled by the tip portion of the thumb 25 of the operator's left hand.

In general, the operating buttons of an endoscope are depressed by the tip portion of the first finger or second finger of the operator's left hand. Particularly, the tip portion of the first finger is used for depressing the operating buttons. In the embodiment of FIG. 7, however, both the first finger 26 and the second finger 22 are used for depressing the operating buttons 17, 18 and 27. In this case, the holding portion 12 is gripped by the third finger 23 and the little finger 24 alone, with the side region of the fourth finger 23 allowed to abut against the rising wall 14. It should be noted that, if the thumb 25 is placed at the optimum position of the operating knob 16, the positions of the first finger 26 and the second finger 22 are adapted for depressing the operating buttons 17 and 18, respectively, because of the relative positional relationship among the operating knob 16, the operating buttons 17, 18 and the rising wall 14. Specifically, the depressing directions of the fingers 26 and 22 are allowed to conform substantially with the axes $O_3$ and $O_4$ of the operating buttons 17 and 18, respectively. As mentioned previously, each of the axes $O_3$ and $O_4$ makes an angle of 102° with the axis $O_1$ of the holding portion 12 in the embodiment of FIG. 7. The angle mentioned should fall within the range of between 100° and 110°.

The relative positional relationship among the operating knob 16, the operating buttons 17, 18 and the rising wall 14 is very important in the present invention. In operating the endoscope, the operating knob 16 is most frequently operated. Naturally, the knob 16 is rotated by the thumb 25. It should be noted in the connection that the third finger 23 abutting against the rising wall 14 is used for temporarily holding the knob 16 stationary. On the other hand, the knob 16 should be located such that the rotation thereof is not obstructed by the third finger 23. To be brief, the positional relationship between the operating knob 16 and the rising wall 14 should be determined to meet the two requirements mentioned above. Also, if the knob 16 is located close to the eyepiece section 15, it is unavoidable for the operating section 1 to be expanded upward because of the positional relationship between the knob 16 and the internal mechanism for controlling the operation of the bending tube 5 (see FIG. 1), with the result that the operating section 1 is rendered bulky and heavy.

The first operating button 17 should be located as close to the rising wall 14 as possible in order to enable the button 17 to be depressed by the second finger 22 without opening sideward the third finger 22 from the third finger 23. Further, the diameter of the operating knob 16 should be determined in view of the force required for rotating the knob 16 and the distance of movement of the thumb 25 required for rotating the knob 16 by a prescribed angle. Incidentally, if the knob 16 is too small in diameter, a large force is required for rotating the knob 16, though the moving distance of the thumb 25 is small, and vice versa.

As described above in detail, the endoscope of the present invention permits the operating buttons to be depressed easily without requiring an unnatural movement of the finger. Thus, the operator does not feel tired.

What is claimed is:

1. An endoscope comprising: an elongated insert section including a distal end portion to be inserted into a body cavity and a proximal end portion; an operation section connected to the proximal end of the insert section, and including a holding portion which is gripped by the third and little finger of a single hand of an operator, a central axis extending along the longitudinal direction of the holding portion and means for permitting operation of the endoscope without requiring unnatural movements of an operator's fingers, said means including a mounting surface located adjacent to the holding portion and within reach of at least one finger of the operator's hand; a rising wall on the operation section between the mounting surface and the holding portion to enable the third finger gripping the holding portion to abut against the rising wall to define a holding position; an eyepiece section mounted on one end portion of the operation section such that the optical axis of the eyepiece section is inclined from the central axis of the holding portion toward the side opposite to that on which the mounting surface is located; said mounting surface having a first end located adjacent to said rising wall and a second end located adjacent to said eyepiece section and being inclined from said first end toward said central axis so that said second end is closer to the central axis than said first end; and operating buttons mounted on the mounting surface to extend outwardly from said inclined mounting surface such that they can be depressed toward said mounting surface in the direction of the central axis of the operating buttons, said inclined mounting surface orienting said buttons such that they are lower in height relative to the central axis of the holding portion as they are positioned further away from the rising wall, said buttons being positioned in a row along the central axis of the holding portion; in which the central axis of the operating buttons are at an angle of between greater than 90° and less than 150° to the central axis of the holding portion wherein the operating buttons are provided on the holding portion in a manner such that the central axis of the operating buttons intersects the central axis of the holding portion at an angle of greater than 90° for access by an operator.

2. The endoscope according to claim 1, wherein the central axes of the operating buttons are parallel with each other and are at an angle of between 90° and 102° to the central axis of the holding portion.

3. The endoscope according to claim 1, wherein the central axes of the operating buttons are at an angle of between 100° and 110° to the central axis of the holding portion.

4. An endoscope comprising: an elongated insert section including a distal end portion to be inserted into a body cavity and a proximal end portion; an operation section connected to the proximal end of the insert section, and means for permitting operation of the endoscope without requiring unnatural movements of an operator's fingers, said means including a holding portion which is selectively gripped by proper fingers including at least the third and little finger of a single hand of an operator, a central axis extending along the longitudinal direction of the holding portion and a mounting surface located adjacent to the holding portion and within reach of at least one finger of the operator's hand; a rising wall on the operation section between the mounting surface and the holding portion to enable the proper finger, close to a thumb, gripping the holding portion to abut against the rising wall to define a holding position; an eyepiece section mounted on one end portion of the operation section such that the optical axis of the eyepiece section is inclined from the central axis of the holding portion toward the side opposite to that on which the mounting surface is located, said mounting surface having a first end located adjacent to said rising wall and a second end located adjacent to said eyepiece section and being inclined from said first end toward said central axis so that said second end is located closer to said central axis than said first end; and operating buttons mounted on the mounting surface to extend outwardly from said mounting surface and being mounted such that they can be depressed in the direction of said mounting surface in the direction of the central axis of the operating buttons, said inclined mounting surface orienting said buttons such that they are lower in height relative to the central axis of the holding portion as they are positioned further away from the rising wall, said buttons being positioned in a row along the central axis of the holding portion; in which the central axis of the operating buttons are at an angle of between greater than 90° and less than 150° to the central axis of the holding portion wherein the operating buttons are provided on the holding portion in a manner such that the central axis of the operating buttons intersects the central axis of the holding portion at an angle of greater than 90° for access by an operator.

* * * * *